(12) United States Patent
Ray et al.

(10) Patent No.: US 6,371,118 B1
(45) Date of Patent: Apr. 16, 2002

(54) BIRTH CONTROL APPARATUS

(76) Inventors: Terry L. Ray, 1118 E. San Angelo Ave., Gilbert, AZ (US) 85234; James W. Zeluff, 11165 Sandy Grove Ave., Las Vegas, NV (US) 89144

( * ) Notice: Subject to any disclaimer, the term of this patent is extended or adjusted under 35 U.S.C. 154(b) by 0 days.

(21) Appl. No.: 09/588,949

(22) Filed: Jun. 7, 2000

(51) Int. Cl.[7] .................................................. A61F 6/06
(52) U.S. Cl. ...................................... 128/830; 128/831
(58) Field of Search ................................. 128/830–841

(56) References Cited

U.S. PATENT DOCUMENTS

| | | |
|---|---|---|
| 404,019 A | 5/1889 | Sperry |
| 2,785,675 A | 3/1957 | Berkman |
| 3,675,639 A | 7/1972 | Cimber |
| 3,680,542 A | 8/1972 | Cimber |
| 3,858,571 A | 1/1975 | Rudloph |
| 3,918,431 A | 11/1975 | Sinnreich |
| 4,365,621 A | 12/1982 | Brundin |
| 4,537,186 A | 8/1985 | Verschoof |
| 4,606,336 A | 8/1986 | Zeluff |
| 4,834,091 A | 5/1989 | Ott |
| 5,601,600 A | 2/1997 | Ton |
| 5,702,421 A | 12/1997 | Schneidt |

FOREIGN PATENT DOCUMENTS

EP            105669          8/1984

*Primary Examiner*—Michael A. Brown
(74) *Attorney, Agent, or Firm*—Parsons & Goltry; Robert A. Parsons; Michael W. Goltry

(57) ABSTRACT

Apparatus for preventing fluid transfer through an opening between an oviduct and a uterine cavity including an insert for insertion into the oviduct through the opening, the insert having a first portion for causing fibroblast ingrowth and a second portion including a biodegradable anchor for securing the insert to the oviduct.

20 Claims, 3 Drawing Sheets

BIRTH CONTROL APPARATUS

FIELD OF THE INVENTION

This invention concerns birth control and, more particularly, apparatus and methods for preventing fluid from passing between an oviduct and a uterus of a female reproductive system.

BACKGROUND OF THE INVENTION

Prescription birth control drugs are expensive. As a result, many people rely on less expensive mechanical devices as a means for inhibiting conception. Nearly all mechanical birth control devices and techniques attempt to block fluid transfer between either the vagina and the uterus or the oviducts and the uterus. By preventing fluid transfer between the uterus and the vagina and/or the oviducts, conception is prevented or at least minimized. Although existing mechanical devices and techniques prove adequate, they are often unreliable and difficult to construct and install.

Thus, there is a need for a device for preventing conception that is easy to construct, easy to install, safe to use and that resists infection over extended periods of continuous use.

SUMMARY OF THE INVENTION

The above problems and others are at least partially solved and the above purposes and others realized in new and improved birth control apparatus comprising an insert positionable in a uterotubal junction between a uterine cavity and an oviduct. The insert has a first portion for promoting fibroblast ingrowth and a second portion having an anchor for securing the insert to the oviduct. The anchor or at least part of the second portion including the anchor is biodegradable.

BRIEF DESCRIPTION OF THE DRAWINGS

Referring to the drawings.

DETAILED DESCRIPTION OF A PREFERRED EMBODIMENT

Figure 1:
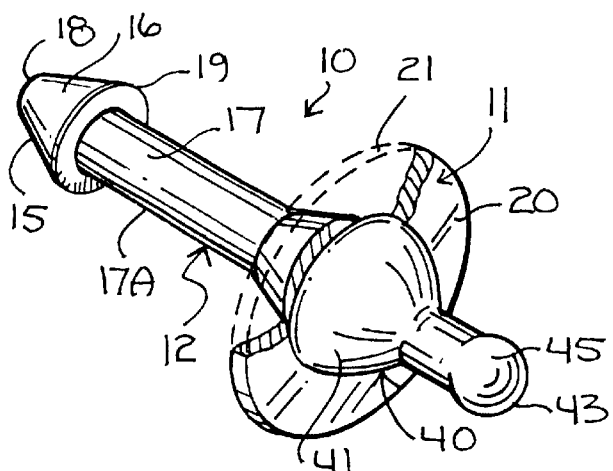
FIG. 1 is a perspective view of birth control apparatus in accordance with the invention.

Turning to the figures, FIG. 1 illustrates a perspective view of birth control apparatus 10. Apparatus 10 prevents fluid transfer between an oviduct and a uterine cavity of a female reproductive system and includes an element for forming a seal at, adjacent or proximate the opening between the oviduct and the uterine cavity and another element for anchoring apparatus 10 to the oviduct to allow the seal to form. With this generally in mind, apparatus 10 is comprised of an insert 12 having a seal 11. Seal 11 may be constructed separately and installed onto insert 12, or formed with insert 12. With the exception of seal 11, insert 12 is substantially or partially constructed of a substantially rigid biocompatible material such as stainless steel, titanium, ceramic, a polybase material or other similar material or combination of materials. Insert 12 includes a shaft 17 having a length, a proximal extremity or end 14, a free or distal extremity or end 15 and an anchor 16. In this embodiment, anchor 16 is an enlargement that is substantially conical and located at or adjacent distal extremity 15. Anchor 16 leads with a substantial point or vertex 18, that is somewhat rounded in this embodiment, and trails with a base or directrix 19 that defines a step angle with shaft 17. Directrix 18 faces proximal extremity 14 and defines a diameter that is greater than outer diameter 17A of shaft 17.

In the present embodiment, seal 11 is comprised of a continuous body 20, which encircles a portion of insert 12 adjacent proximal extremity 14. Body 20 includes an outer diameter or continuous extremity 21 that is greater than that of directrix 19 and shaft 17. Body 20 is configured, fabricated of, coated or otherwise provided with a material that promotes fibroblast ingrowth, such as polytetrafluoroethylene (PTFE) plastic, which is a well-known existing material sold under the trademark TEFLON. Appropriate porous PTFE materials are commercially available and may be produced by the process described in Japanese Patent Publication No. 135,60/67 and U.S. Pat. No. 3,953,566, which are incorporated by reference herein. Other acceptable porous materials manufactured and sold under the trademarks PROPLAST or GORTEX may also be used for body 20. Further included in a list of preferred materials for body 20 is cotton, polyethylene, polyester, and/or silk mesh. In one embodiment, body 20 may be configured with a micro porous fibrous structure consisting of small fibers and nodes connected together. Similar expanded PTFE products are presently in use for vascular prostheses and typically include pore sizes on the order of two microns or greater. Typical pore sizes for most effective utilization in vascular prostheses generally fall within the range of among approximately five to ten microns.

Figure 2:
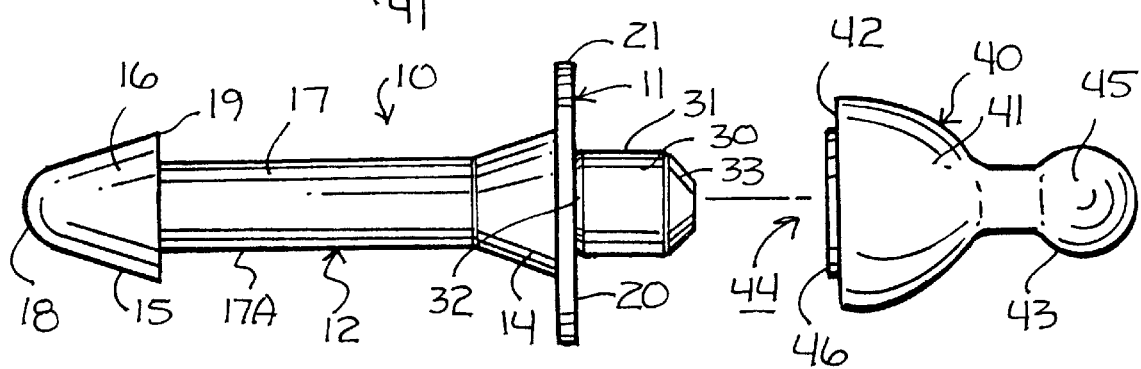
FIG. 2 is an exploded side view of the apparatus of FIG. 1.

Regarding FIG. 2, insert 12 has an extension 30 that extends away from proximal extremity 14. Extension 30 defines an outer diameter or continuous extremity 31 that is substantially equal to outer diameter 17A of shaft 17, a continuous beveled edge 32 facing proximal extremity 14 and a continuous beveled edge 33 spaced and facing away from proximal extremity 14. The outer diameter of extension 30 may be of any desired size. A cap 40 is also provided, which is comprised of a body 41 having an inner end 42, an outer end 43, a socket 44 extending into inner end 42 and a ball joint 45 positioned, in this embodiment, adjacent outer end 42. A continuous extension or bead 46 extends away from inner end 42, which bounds the opening leading to socket 44. Cap 40 is designed to fit onto extension 30 in a supported condition and socket 44 is sized to so accommodate extension 30. Beveled edge 33 allows extension 30 to easily guide into socket 44, and the fit between extension 30 and socket 44 is snug, like a substantial press fit. When properly installed, bead 46 extends into body 20 displacing it against beveled edge 32 to form a seal between cap 40 and extension 30 and, more particularly, between bead 46 and beveled edge 32.

Figure 3:
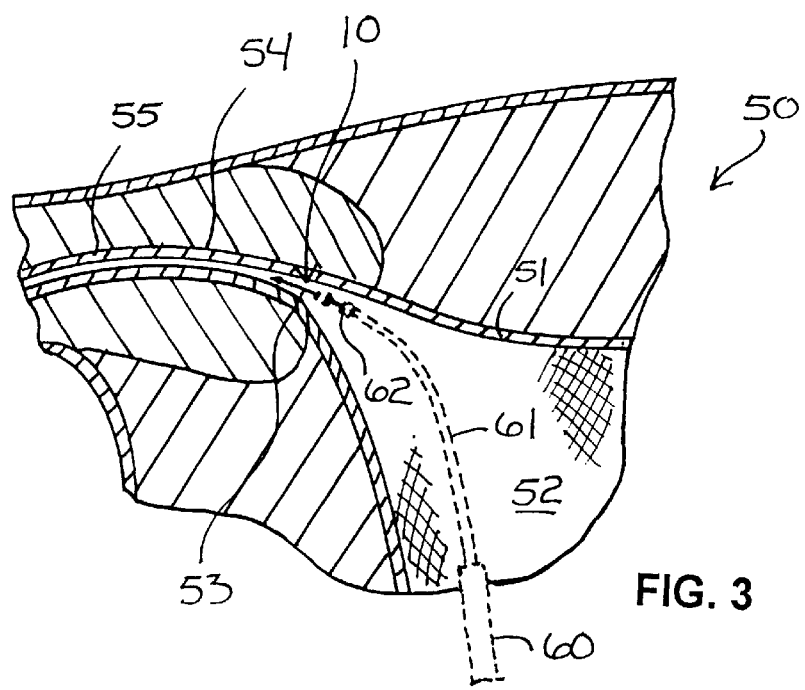
FIG. 3 is a view showing the apparatus of FIG. 1 as it would appear being installed.

Looking now to FIG. 3, shown is fragmented sectional view of a female reproductive system 50 including a uterus 51 bounding a uterine cavity 52, and an opening 53 leading to an isthmus 54 of an oviduct 55. Skilled artisans often refer to opening 53 that is generally between uterine cavity 52 and oviduct 55 as the uterotubal junction. To install apparatus 10, a guide catheter 60 may be maneuvered into uterine cavity 52 by way of the vagina and the cervix. Catheter 60 is preferably flexible, which allows it to be easily maneuvered into the uterine cavity 52. Catheter 60 may comprise the operating channel of a hysteroscope, a commercially available device used by gynecologists for examining and operating on the female reproductive system. A conventional hysteroscope typically includes three parallel oriented channels that run longitudinally along a given length of the device. One of these channels provides a source of illumination, another of the channels includes a fiberoptic bundle having optics for viewing, and the final one of the channels houses a flexible guide 61 having flexible jaws or tongs 62 that is capable of engaging and gripping things, such as ball joint 45. Guide 61 includes a mechanism that a physician may operate for moving tongs 62 between an open condition and a closed condition for engaging ball joint 45. By maneuvering guide 61 through catheter 60, apparatus 10 may be inserted, distal extremity 15 first, into and through opening 53. Ball joint 45 permits apparatus 10 to move, deflect or articulate as needed relative to tongs 62 for providing a natural and easy alignment and insertion of insert 12 into oviduct 55 through opening 53. The fiberoptic bundle and the illuminating ability of catheter 60 allows the physician to visually identify opening 53.

Figure 4:
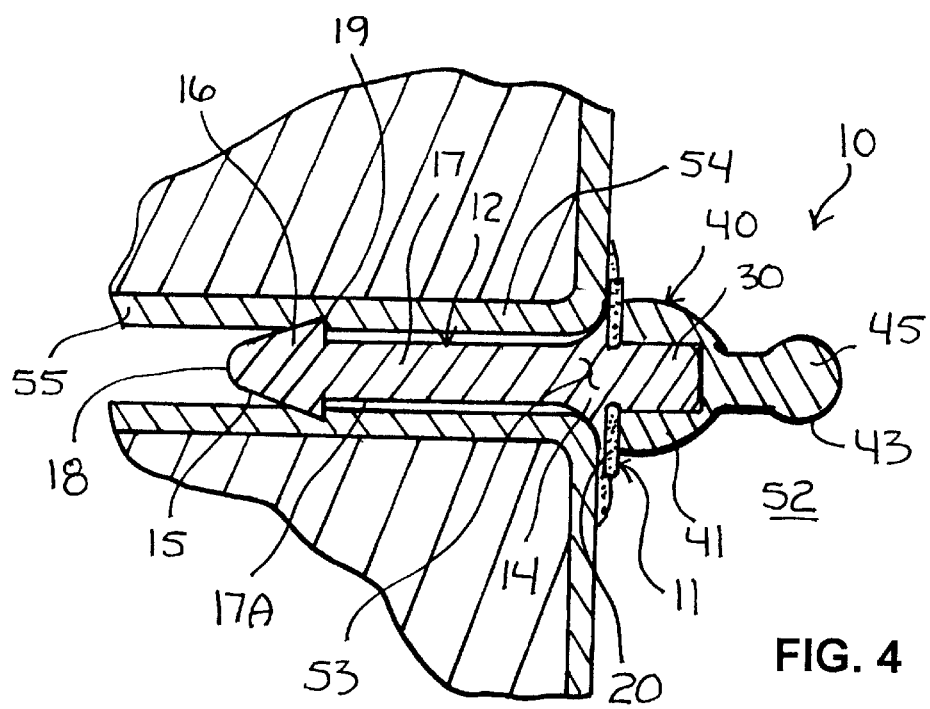
FIG. 4 is a view showing the apparatus of FIG. 1 as it would appear installed in a female reproductive system.

With vertex 18 facing opening 53, insert may be easily inserted into oviduct 55 through opening 53. The blunt or rounded vertex 18 provides for a smooth insertion into oviduct 55 through opening 53. Although directrix 19 is enlarged, it will readily pass into oviduct 55 through opening 53 as it trails vertex 18. However, seal 11, in this specific embodiment is of a size too great to pass through opening 53, and engages against the surface of uterine tissue leading to and defining opening 53 as shown in FIG. 4, which generally defines at least a portion of the uterotubal junction. Insert 12 maintains a desired alignment between seal 11 and the uterine tissue leading to and defining opening 53. Once insert 12 is inserted into oviduct 55 with seal 11 positioned against the uterine tissue leading to and defining opening 53, fibroblast ingrowth between that surrounding uterine tissue and seal 11 begins to form an initially weak but progressively stronger bond between seal 11 and the uterine tissue. Directrix 19 is directed against and engages or impinges into the inner surface of oviduct 55. Because directrix 19 is directed toward opening 53, insert 12 cannot be easily moved out of oviduct 55 for directrix 19 digging or impinging into oviduct 55 tissue, which prevents insert 12 from inadvertently falling away from oviduct 55. Accordingly, anchor 16, and especially directrix 19, holds insert 12 in place so that seal 11 can accept fibroblast ingrowth to provide a seal at the uterotubal junction and thus fluid isolation between oviduct 55 and uterine cavity 52. The seal between bead 46 and beveled edge 32 further ensures fluid isolation between oviduct 55 and uterine cavity 52. Although anchor 16 is positioned at or adjacent distal extremity 15, it may be positioned at other locations along insert 12 between the proximal and distal extremities 14 and 15. Anchor 16 may be provided in any desired size suitable for providing the described impingement against the inner surface of an oviduct.

In this embodiment, anchor 16 is biodegradable and becomes absorbed, flushed or eliminated by the human body over a certain period of time after installation into the oviduct. In this regard, anchor 16 is designed to provide a securement to the oviduct for a time sufficient for fibroblast ingrowth to manifest to a degree sufficient to cause a substantial seal proximate the uterotubal junction. Once this seal is formed, the usefulness of anchor 16 is depleted and it biodegrades or becomes eliminated by the body, leaving the fibroblast seal at or proximate the uterotubal junction. The biodegradable material used to form anchor 16 may comprise any suitable natural and/or synthetic biocompatible and biodegradable/bioabsorbable material such as any one or more of a variety of biodegradable polymers such as polyglycolide and polyactide, and copolymers of glycolide and lactide, trimethylene carbonate, and caprolactone and the like. Other biodegradable and biocompatible materials will readily occur to the skilled artisan.

To remove apparatus 10 after fibroblast ingrowth is complete, ball joint 45 is taken, such as with tongs 62, and apparatus 10 forcibly removed. Because uterine and oviduct tissue is considerably resilient, tissue damage caused by the forcible removable of apparatus 10 heals very quickly.

Seal 11 can be configured and arranged with insert 12 (as either a part of insert 12 or as a separate element mounted to or otherwise carried by insert 12) in a variety of ways for accepting and/or promoting fibroblast ingrowth at any position at or adjacent the uterotubal junction including not only the uterine tissue leading to and defining opening 53, but also to the tissue defining opening and extending at least partially into the oviduct. The purpose of anchor 16 is simply to hold insert 12 in place until the seal is formed.

Figure 5:
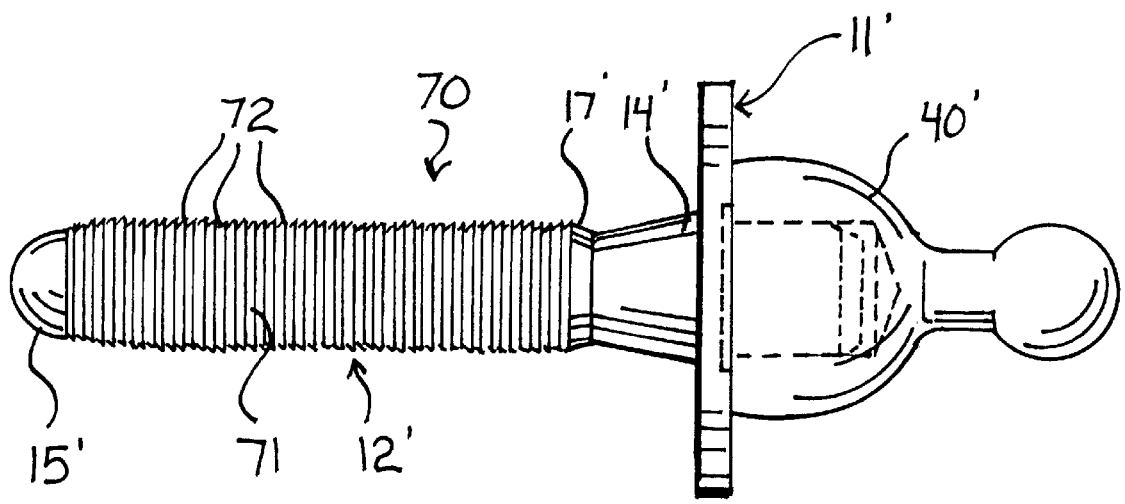
FIG. 5 is a side view of another embodiment of an birth control apparatus in accordance with the invention.

FIG. 5 illustrates an alternate embodiment of apparatus 70 for preventing fluid transfer between an oviduct and a uterine cavity of a female reproductive system. Apparatus 70 is substantially identical to apparatus 10 in structure and function, and includes substantially the same elements. Accordingly, the reference characters used to describe apparatus 10 will also be used to describe apparatus 70, but only to the extent of their common structural components. For clarity, common reference characters used to describe apparatus 70 will include a prime ("'") symbol. In this regard, apparatus 70 includes seal 11', insert 12', proximal extremity 14', distal extremity 15', shaft 17' and cap 40' as previously described. In this embodiment, shaft 17' includes an anchor that is comprised of a textured outer surface 71 between the proximal and distal extremities 14' and 15'. In this embodiment, textured outer surface 71 is continuous and is defined by a plurality of teeth 72. Teeth 72 are aligned in series between the proximal and distal extremities 14' and 15'. Each one of teeth 72 is continuous and is directed or slanted toward proximal extremity 14'. Because teeth 72 are each directed toward proximal extremity 14', insert 12 may easily be inserted into an oviduct in a direction leading with distal extremity 15'. Distal extremity 15' is defined as somewhat rounded or blunt, which facilitates easy insertion into an oviduct. When positioned in an oviduct, teeth 72 impinge against the inner surface of the oviduct and direct toward the opening leading to the oviduct. As a result, insert 12' cannot be easily moved out of the oviduct for the teeth 72 digging or impinging into the oviduct 55 tissue, which prevents insert 12' from inadvertently falling away from the oviduct. Like anchor 16, teeth 72 are biodegradable and hold insert 12' in place until a fibroblast seal has formed by way of seal 11'.

Attention is now directed to FIGS. 6 through 10, which illustrate various embodiments of apparatus for preventing fluid transfer between an oviduct and a uterine cavity of a female reproductive system. The embodiments in FIGS. 6 through 10 are common, in that they are each comprised of two main elements including one for forming a seal at or adjacent the uterotubal junction and another for anchoring the apparatus to the oviduct for allowing the seal to form. Accordingly, the apparatus in FIGS. 6 through 10 are each given a common reference character 100. The apparatus shown in FIGS. 6 through 10 are each substantially identical to apparatus 10 in structure and function, and include substantially the same elements. Accordingly, the reference characters used to describe apparatus 10 will also be used to describe the apparatus in FIGS. 6 through 10, but only to the extent of their common structural components. For clarity, common reference characters used to describe the apparatus in FIGS. 6 through 10 will include a prime ("'") symbol.

Figure 6:
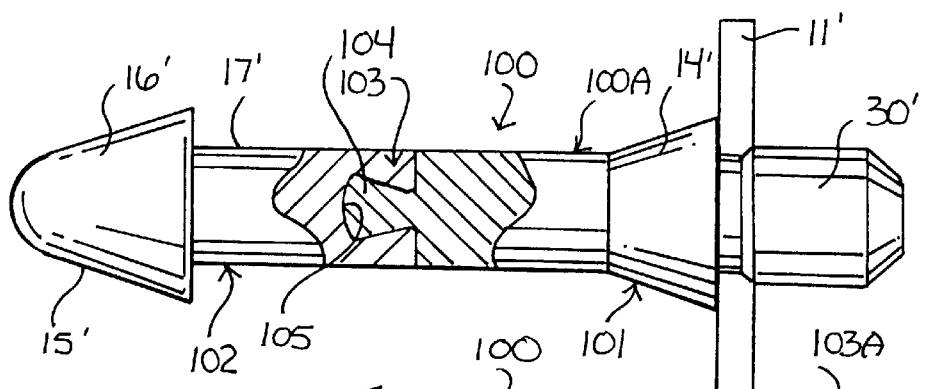
FIGS. 6 through 10 illustrate various embodiments of birth control apparatus each in accordance with the invention.
Figure 7:
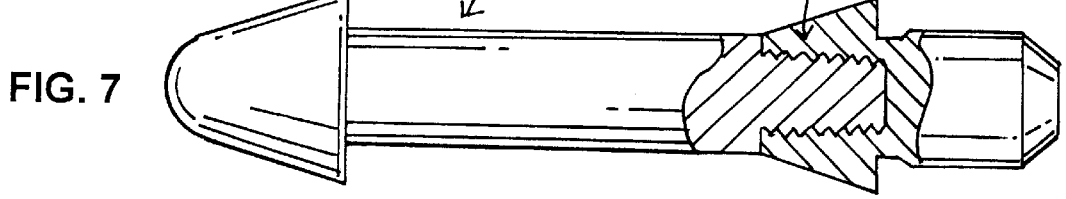
Figure 8:
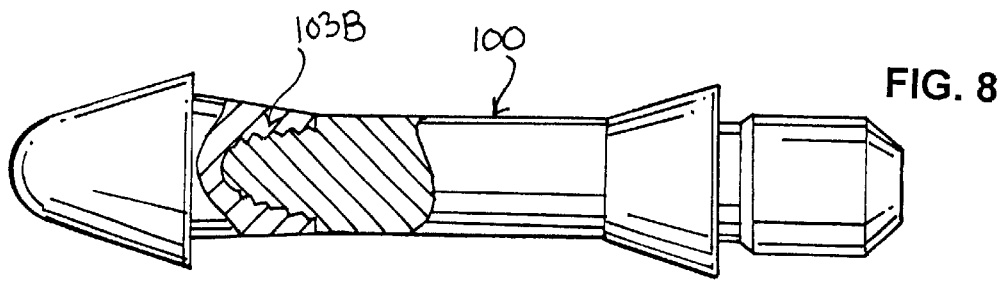
Figure 9:
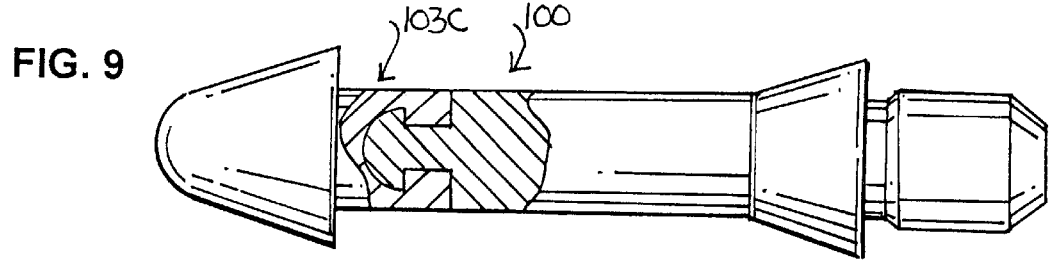
Figure 10:
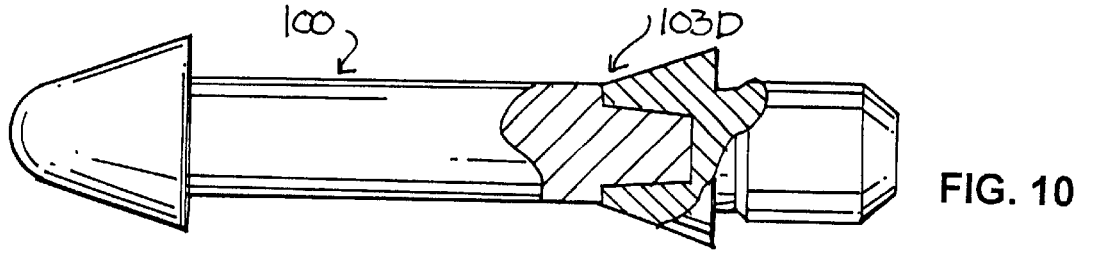

With this in mind, attention is directed specifically to FIG. 6, which illustrates a side view of apparatus 100 for preventing fluid transfer between an oviduct and a uterine cavity of a female reproductive system. Apparatus 100 is comprised of an insert 100A having a sealing element 101 for forming a seal generally at, proximate or adjacent the uterotubal junction and an anchoring element 102 for anchoring apparatus 100 to the oviduct for allowing the seal to form. Sealing element 101 is joined to anchoring element 102 with an engagement structure 103. Like apparatus 10, apparatus 100 (which is also shown in FIGS. 7–10) includes a proximal end or extremity 14', a distal end or extremity 15', an anchor 16', a shaft 17', an extension 30' and a seal 11'. Although anchor 16' is shown as an enlargement located at distal end 15', it may be located at other positions, and it may have other physical forms including, for instance, a textured outer surface of shaft 17' like that set forth in connection with apparatus 70 discussed in combination with FIG. 5 or other suit. In addition to or in lieu of seal 11', part of or all of sealing element 101 may be configured and/or provided with or constructed of a material that promotes fibroblast ingrowth.

In FIG. 6, engagement structure 103 comprises a male engagement element 104 of sealing element 101 and a female engagement element 105 of anchoring element 102 and these may be reversed. Although engagement structure 103 is shown located at a substantially intermediate location between proximal and distal extremities 14' and 15', it may be located at or adjacent proximal end 14' or at or adjacent distal end 15'. Anchoring element 102 is constructed of a biodegradable material that eventually degrades or otherwise becomes absorbed, flushed or eliminated by the human body over an extended period of time after installation into the oviduct. Should anchoring element 102 include anchor 16', as opposed to a textured out surface of shaft 17', only anchor 16' may be constructed of such a biodegradable material. Anchoring element 102 is designed to provide a securement to the oviduct for a time sufficient for fibroblast ingrowth to manifest to a degree sufficient to cause a substantial seal proximate the uterotubal junction. Once this seal is formed, the usefulness of anchoring element 102 is depleted and it or its anchor 16' biodegrades and becomes absorbed, flushed or eliminated by the body, leaving sealing element 101 and the seal proximate the uterotubal junction. The biodegradable material used to form anchoring element 102 or anchor 16' of anchoring element 102 may comprise any suitable natural and/or synthetic biocompatible and biodegradable/bioabsorbable material such as any one or more of a variety of biodegradable polymers such as polyglycolide and polyactide, and copolymers of glycolide and lactide, trimethylene carbonate, and caprolactone and the like. Other biodegradable and biocompatible materials will readily occur to the skilled artisan. A biodegradable adhesive may be used for further securing male engagement element 104 to female engagement element 105 if desired, as is the case with the ensuing alternate embodiments. Should a user desire, an adhesive (whether biodegradable or not) may be alone used for engaging together elements 101 and 102 without the aid of any additional engagement structure.

As a matter of illustration, FIGS. 7 through 10 illustrate apparatus 100 with various threaded and non-threaded male and female engagement pairs 103A–103D, respectively, for facilitating engagement between sealing and anchoring elements 101 and 120. The positioning of these pairs of engagement elements can be reversed and positioned at various locations at and between the proximal and distal extremities.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Apparatus for preventing fluid transfer through an opening between an oviduct and a uterine cavity comprising:
   an insert for insertion into the oviduct through the opening;
   the insert having a first portion for causing fibroblast ingrowth and a second portion including a biodegradable anchor for securing the insert to the oviduct.

2. Apparatus of claim 1, wherein the anchor allows the insert to be inserted into the opening and the oviduct and inhibits the insert from falling away from the oviduct through the opening.

3. Apparatus of claim 1, wherein the anchor comprises an enlargement.

4. Apparatus of claim 1, wherein the anchor comprises a substantially conical body.

5. Apparatus of claim 1, wherein at least a part of the first portion is formed of a biocompatible material that causes ingrowth of fibroblastic tissue.

6. Apparatus for preventing fluid transfer through an opening between an oviduct and a uterine cavity comprising:
   an insert for insertion into the oviduct through the opening;
   the insert having a first portion for causing fibroblast ingrowth and a second portion including an anchor for securing the insert to the oviduct;
   wherein at least a part of the second portion including the anchor is biodegradable.

7. Apparatus of claim 6, wherein the anchor allows the insert to be inserted into the opening and the oviduct and inhibits the insert from falling away from the oviduct through the opening.

8. Apparatus of claim 6, wherein the anchor comprises an enlargement.

9. Apparatus of claim 6, wherein the anchor comprises a substantially conical body.

10. Apparatus of claim 6, wherein at least a part of the first portion is formed of a biocompatible material that causes ingrowth of fibroblastic tissue.

11. Apparatus for preventing fluid transfer through a uterotubal junction between an oviduct and a uterine cavity comprising:
    an insert positionable in a uterotubal junction between a uterine cavity and an oviduct;
    the insert having a first portion for causing fibroblast ingrowth at the uterotubal junction and a second portion including a biodegradable anchor for securing the insert to the oviduct.

12. Apparatus of claim 11, wherein the anchor allows the insert to be inserted into the oviduct and inhibits the insert from falling away from the oviduct through the uterotubal junction.

13. Apparatus of claim 11, wherein the anchor comprises an enlargement.

14. Apparatus of claim 11, wherein the anchor comprises a substantially conical body.

15. Apparatus of claim 11, wherein at least a part of the first portion is formed of a biocompatible material that causes ingrowth of fibroblastic tissue.

16. Apparatus for preventing fluid transfer through an opening between an oviduct and a uterine cavity comprising:

an insert positionable in a uterotubal junction between a uterine cavity and an oviduct;

a first element of the insert for causing fibroblast ingrowth; and a second element of the insert including an anchor for securing the insert to the oviduct;

wherein at least a part of the second element including the anchor is biodegradable.

17. Apparatus of claim 16, wherein the anchor allows the insert to pass into the through the opening and inhibits the insert from falling away from the oviduct through the opening.

18. Apparatus of claim 16, wherein the anchor comprises an enlargement.

19. Apparatus of claim 16, wherein the anchor comprises a substantially conical body.

20. Apparatus of claim 16, wherein at least a part of the first portion is formed of a biocompatible material that causes ingrowth of fibroblastic tissue.

* * * * *